United States Patent [19]

Luber et al.

[11] Patent Number: 5,697,368

[45] Date of Patent: Dec. 16, 1997

[54] PROCESS FOR THE OPERATION OF AN OPERATION MICROSCOPE

[75] Inventors: Joachim Luber, Essingen-Forst; Arvids Mackevics, Unterkochen, both of Germany

[73] Assignee: Carl-Zeiss-Stiftung, Heidenheim, Germany

[21] Appl. No.: 314,130

[22] Filed: Sep. 29, 1994

[30] Foreign Application Priority Data

May 7, 1994 [DE] Germany .......................... 44 16 229.4

[51] Int. Cl.⁶ .................................................. A61B 5/05
[52] U.S. Cl. ..................................................... 128/653.1
[58] Field of Search ........................ 128/653.1, 665; 364/413.13, 413.14, 413.22

[56] References Cited

U.S. PATENT DOCUMENTS

| 4,722,056 | 1/1988 | Roberts et al. |  |
|---|---|---|---|
| 4,835,690 | 5/1989 | Gangarosa et al. | 364/413.13 |
| 4,989,253 | 1/1991 | Liang et al. | 128/897 |
| 5,215,095 | 6/1993 | Macvicar et al. | 128/665 |
| 5,261,404 | 11/1993 | Mick et al. | 364/413.13 |
| 5,273,039 | 12/1993 | Fujiwara et al. | 128/653.1 |
| 5,415,167 | 5/1995 | Wilk | 128/653.1 |
| 5,417,210 | 5/1995 | Funda et al. | 128/653.1 |
| 5,531,520 | 7/1996 | Grimson et al. | 364/413.14 |

FOREIGN PATENT DOCUMENTS 4304571  8/1994  Germany .

*Primary Examiner*—Brian L. Casler

[57] ABSTRACT

For the use of an Operation Microscope, in computer-supported stereotactic surgery, a set of preoperative diagnostic data of a patient is first generated by means of an image-forming preoperative diagnostic procedure. The surgeon then plans the operation path on a central control unit and determines which of the stored diagnostic images are to be reflected into the observation optics of the operation microscope. During the operation, the operation microscope, arranged on a motorized support system, is caused to travel in a motorized manner along the established operation path, and the diagnostic images corresponding to the prior selection are selectively reflected into the observation optics of the operation microscope without a correlation having to be carried out of the respective individual coordinate systems.

10 Claims, 2 Drawing Sheets

PROCESS FOR THE OPERATION OF AN OPERATION MICROSCOPE

BACKGROUND OF THE INVENTION

1. Field of the Invention

The present invention relates to a process for the operation of an operation microscope in computer-supported stereotactic surgery. In particular, the aim here is the use of preoperatively generated diagnostic images for orientation during the operation itself.

2. Relevant Prior Art

An operation microscope for use in computer-supported stereotactic surgery is known from U.S. Pat. No. 4,722,056, in which there takes place during an operation the reflecting of operatively generated diagnostic images into the observation beam paths of the operation microscope, whereby there results, for the observer, the superposition of diagnostic images and the plane of the field of view. An operation microscope of this kind finds a typical application in neurosurgery, for example.

For the operation of an operation microscope according to U.S. Pat. No. 4,722,056 there is however required an expensive correlation of the coordinate systems for the patient, the operation microscope and the images, in order to guarantee in each case that the diagnostic images corresponding to the present field of view are reflected into the observation optics of the operation microscope. Thus the position of the field of view at any given time during the operation must be practically continuously monitored, which takes place by the position determination of the operation microscope by means of an ultrasonic transducer system, and by means of the currently set optical data such as focal length, etc. There thus results, in all, a complex overall system.

Aside from the expensive, continuously required correlation of the respective coordinate systems, the reflecting of related preoperative diagnostic images into the field of view, or the corresponding superposition, however does not yet represent the optimum orientation information for the operating surgeon. Namely, a problem here is the fact that the diagnostic images which have been reflected in also have to be magnified, corresponding to the respective magnification of the operation microscope optics. Due to the resolution at present possible in preoperative imaging diagnostic procedures, an advantage for the operating surgeon does not necessarily result when such original images are directly superposed on, or reflected into, the field of view at an appropriate magnification. Further aids to orientation are therefore required for the surgeon who observes the operation field through the operation microscope.

SUMMARY OF THE INVENTION

The present invention has as its object a process for the operation of an operation microscope in computer-supported, stereotactic surgery which ensures a sufficient orientation of the operating surgeon during the operation and brings forward from preoperatively produced diagnostic procedures, at the least possible expense, the information for the optimization of orientation. Furthermore, it is to be possible to also use data which have been acquired during the operation.

This object is achieved by a process with the following features: generating a diagnostic data set by means of an image-forming preoperative diagnostic procedure, storing the diagnostic data set in digitized form in an image database, planning a surgical operation on a central control unit by means of the diagnostic data set, thereby establishing an operation path, selecting two-dimensional diagnostic images according to the operation path from the diagnostic data set at freely selectable spacings and orientations, and causing the operation microscope to travel along the operation path in a defined, motorized manner during the surgical operation and selectively reflecting the diagnostic images into the observation optics of the operation microscope independently of the position of the field of view of the operation microscope. Advantageous embodiments of the process according to the invention are the subject of the dependent claims.

In contrast to the known process from U.S. Pat. No. 4,722,056, in the process according to the invention the continuous and expensive correlation of the plane of the field of view and the preoperatively produced diagnostic data, or of the corresponding diagnostic images, during the operation itself, is discarded.

On the contrary, a defined operation path, based on the preoperatively generated diagnostic data, is established by the surgeon before the operation proper, and during the operation he advances on it, e.g. towards a tumor. Before the operation, the surgeon chooses, from the diagnostic data deposited in digitized form in an image database, the diagnostic images which are of interest to him, and which correspond to two-dimensional sectional images which advantageously lie on the operation path. The correspondingly selected diagnostic images are then stored again in the image database. Planning of the operation thus takes place on a central control unit.

During the operation proper, the diagnostic images according to the previously defined sequence are selectively reflected into the observation optics of the operation microscope, however without always undertaking an explicit association with the field of view at present inspected.

As regards the reflecting into the observation optics of the operation microscope, the choice is then possible between a superposition of the diagnostic images on the exact field of view concerned and also the mere observation of the selected diagnostic images.

Advantageously, certain positional information for the respective diagnostic images is also reflected into the observation optics together with the selected diagnostic images, in order to make possible to the surgeon at least a coarse spatial allocation when observing these images.

The operation microscope is attached to a motorized support system on which it can be definitively positioned in at least three spatial degrees of freedom.

The process according to the invention now not only makes it possible for the surgeon to observe the respective present diagnostic image corresponding to the field of view; what is more, he can also, already before the operation, select from a diverse assortment those diagnostic images which he would want to inspect during the operation.

It is here further possible for the operating surgeon to manipulate the diagnostic images, once selected, before the operation; for example, this can take place by drawing in certain contours of interest in the selected diagnostic images.

In addition to this, a series of information specific to the patient can also be stored together with the selected diagnostic images and can be presented to the surgeon as supporting information, reflected into the field of view of the operation microscope during the operation.

It has further been found to be advantageous to also represent on a separate monitor the images perceived by the operating surgeon, including the superposed diagnostic images, and thus to place this information at the disposal of assisting personnel.

DESCRIPTION OF THE DRAWINGS

Further advantages and particulars of the process according to the invention will become apparent from the following description of embodiment examples of the process with reference to the accompanying Figures.

FIG. 2b shows the positions of the selected diagnostic images along the operation path in the representation of FIG. 2a;

DETAILED DESCRIPTION OF PREFERRED EMBODIMENTS

Figure 1:
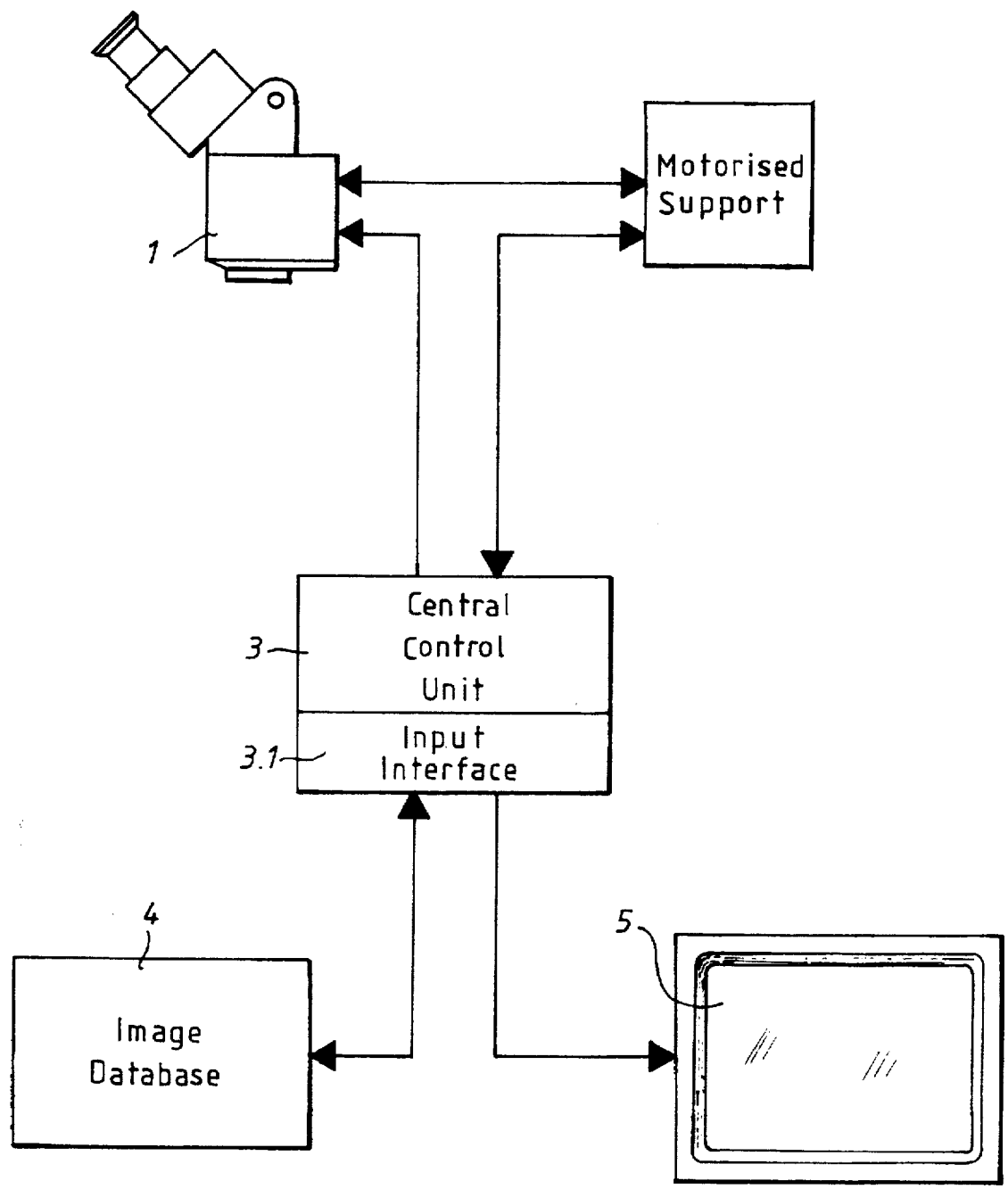
FIG. 1 shows a block circuit diagram with individual components for carrying out the process according to the invention.

A block circuit diagram is shown in FIG. 1, with important components required for carrying out the process according to the invention. An operation microscope (1) is provided here, which is arranged on a motorized support system (2), which is shown only schematically. A defined positioning of the operation microscope (1) according to coordinates in up to six spatial degrees of freedom is possible by means of the motorized support system (2). The multi-articulated, motorized support system, as shown, for example, in the applicant's DE [German Patent] 4,202,922, includes among other things the encoders associated with the respective joints, so that it is possible for the central control unit (3) of the overall system to make a continuous determination of the actual coordinate position of the operation microscope (1), together with the known geometric information of the overall system.

The operation microscope has an essentially known optical construction and includes, among other things, a reflecting device, by means of which it is possible to reflect externally generated images via conventional beamsplitter apparatus into at least one observation beam path.

Furthermore, a previously produced set of preoperative diagnostic data is provided, and is stored, for example, in an image database (4). The digitized diagnostic data sets, which were generated by, e.g., NMR, CT or X-ray investigations before the operation proper, are stored in the image database (4). Both the original images and also images which have been manipulated by the surgeon can be stored here. By "manipulated images" it is to be understood here that, e.g., images or data sets have been stored which contain only marked-in contours of certain anatomical details. Simultaneously, however, the exact spatial position of the diagnostic images which have been manipulated in this manner is known relative to the patient coordinate system.

The central control unit (3) takes over the continuous monitoring of the coordinates of the operation microscope (1) and likewise the processing of the digitized diagnosis data sets in the image database (4), and for this purpose also includes an input interface (3.1), by means of which the surgeon carries out operation planning on the central control unit (3).

Moreover a display (5) is provided which makes possible the observation and manipulation of the images deposited in the image database (4). Likewise, the image information to be reflected into the operation microscope (1) can be observed by the assisting personnel during the operation on a larger scale by means of the display (5).

The process according to the invention for the operation of an operation microscope will now be described in more detail with reference to FIGS. 2a–2c.

Figure 2A:
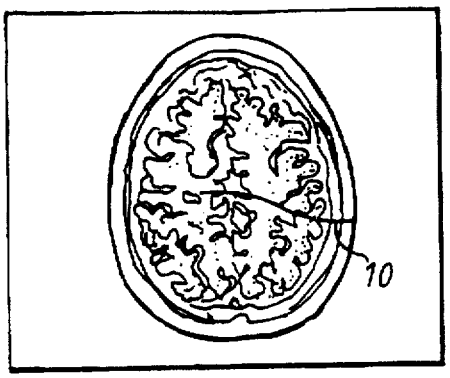
FIG. 2a shows a possible representation of a preoperatively generated diagnostic image on a display which is made use of for operation planning.

FIG. 2a shows a preoperatively generated diagnostic image which was recovered in a known manner by means of a computer tomography apparatus and was stored in digitized form in the database. A two-dimensional sectional image through the human cranium is shown in FIG. 2a in a view from above. Besides this selected image, diagnostic images through diverse further planes in the human head can be reconstructed by means of known image processing procedures from the recorded diagnostic data set.

The planned operation path (10) is already marked and established by the surgeon in the diagnostic image before the operation proper, as is necessary, e.g., in order to be able to penetrate a tumor in the brain. The central control unit connected to the database records the operation path (10), after its planning has been completed, with respect to coordinates.

The surgeon now plans, in the process according to the invention, likewise before the operation proper, which diagnostic images he may wish to have reflected into the operation microscope during the operation proper. Four such desired diagnostic images (1, . . . 4), and their respective position along the operation path, are shown in FIG. 2b. Both the position and the orientation of these diagnostic images relative to the operation path can here be selected in a defined manner by the surgeon. In the embodiment example shown, diagnostic images, oriented parallel, were selected which follow each other at constant spacings.

It should once more be stressed that both these spacings and also the spatial orientation of these diagnostic images can be freely selected by the surgeon before the operation.

Figure 2B:
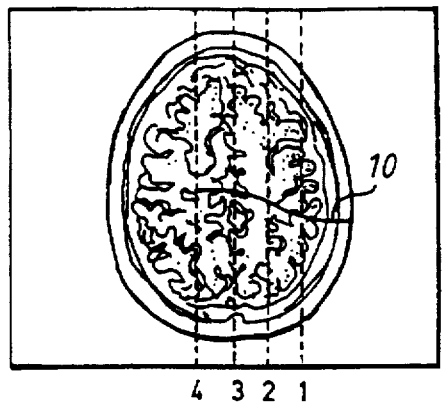
Figure 2C:
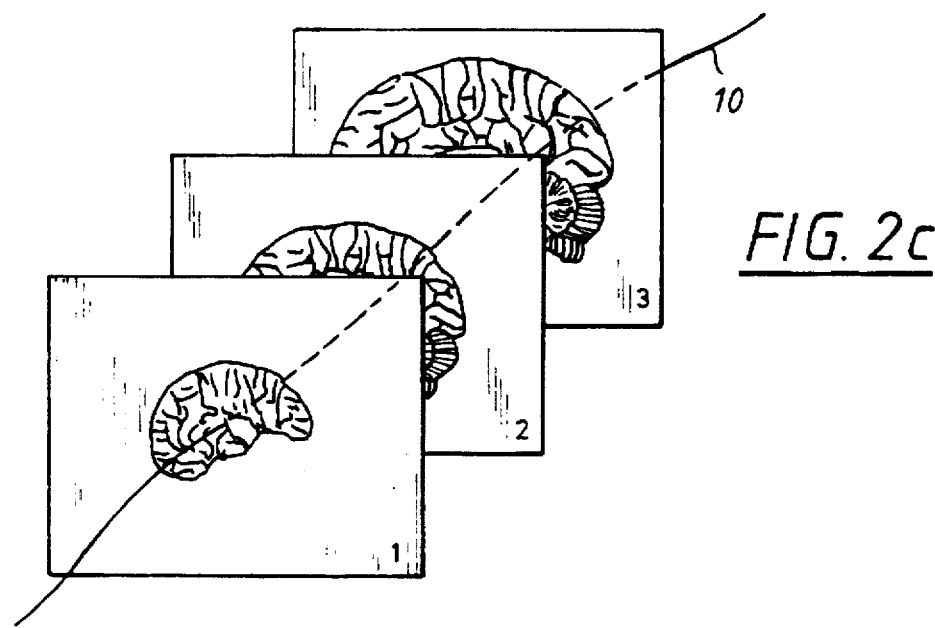
FIG. 2c shows a schematized perspective overall view of the positions of the selected diagnostic images along the operation path in FIG. 2b.

A spatial view, with the planned operation path (10) and three of the four selected diagnostic images (1, 2, 3), is shown in FIG. 2c.

The reflecting of the diagnostic images, once selected, into the observation optics of the operation microscope used now no longer takes place, according to the invention, in a defined dependence on the present position of the field of view, as in U.S. Pat. No. 4,722,056; on the contrary, it is possible for the surgeon to selectively call up and reflect the previously selected images in at any time, i.e., at any place in the operation path. For example, by pressing a button during the operation, the previously established image data set with the four diagnostic images can be reflected in or entered.

Certain positional information for the diagnostic images is then advantageously entered simultaneously with the respective diagnostic images, and then makes possible the positional allocation by the surgeon of the images which have been reflected in. Such positional information can be given, for example, in the form of image numbers, which then make possible, with an approximately constant selected image spacing, a depth allocation and therewith also a rapid orientation along the planned operation path.

Besides the superposed representation of diagnostic images and the present observed field of view, in an alternative mode of operation of the process according to the invention it is possible to reflect solely the diagnostic images into the observation optics of the microscope and to dispense with the superposed representation with the field of view. For this purpose it is only necessary to stop down the beam paths coming from the object by means of known shutter elements. Advantageously, it is possible for the surgeon to choose during the operation between the superposed representation and the mere observation of the diagnostic images which have been reflected in.

The diagnostic images shown in FIGS. 2a–2c correspond to the original images from the preoperative diagnostic procedure, as described above. However, it is occasionally advantageous to reflect images in, which have only a reduced information content in comparison with the original images. Such a reduced information content can, for example, consist of the reflecting in of contours of certain anatomical details or the like.

Figure 3A:
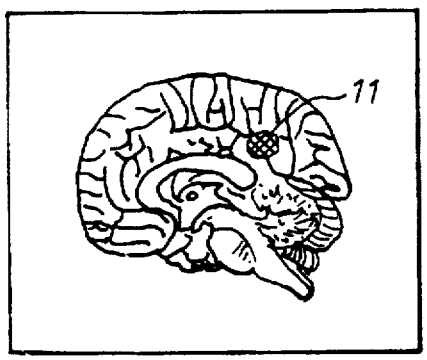
FIG. 3a shows a selected diagnostic image which is manipulated before the operation.
Figure 3B:
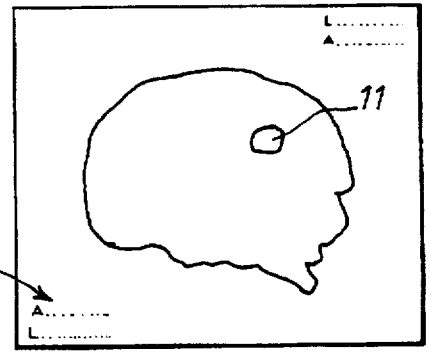
FIG. 3b shows the manipulated diagnostic image of FIG. 3a, which shows only the marked contours of anatomic details of interest.

The manner in which such contours are generated, for example from the original diagnostic image which has a defined spatial relationship to the patient, is shown in FIGS. 3a and 3b. A tumor (11) in the original diagnostic image is there graphically marked, e.g. by means of a suitable computer mouse, and a modified image according to FIG. 3b is produced, which now shows only this contour of the tumor (11). Only this image with the tumor contour (11) is then reflected into the field of view of the operation microscope, while the rest of the anatomical information is deliberately dispensed with.

Further information fields (12) in the diagnostic image which has been reflected in are likewise shown in FIG. 3b, in which both special, patient-specific information is inserted and also the abovementioned positional information for the respective diagnostic image, making possible a spatial allocation of this image by the surgeon during the operation. There can be entered into the information fields (12), for example, the patient's name, information on the present state of the equipment or else certain intra-operative patient information which is continuously sensed during the course of the operation, such as blood pressure, pulse rate, etc. It is of course also possible to reflect in, in a suitable graphical form, intra-operative responses to stimulation processes.

Possible positional information to be reflected in, are the image number from the selected choice of diagnostic images, or else the distance to the following or the preceding image, etc.

Moreover, for optimizing of orientation, it is possible for the surgeon to reflect graphical information in, superposed on the field of view and indicating to the surgeon whether he is still on the originally planned operation path. For this purpose it is necessary to sense the exact observed point relative to coordinates and to compare whether this point still lies on the actually planned operation path. The sensing of this point relative to coordinates can then perhaps take place with an operation microscope such as that shown in the Applicant's DE 4,134,481. According to whether the operating surgeon is still on the correct, planned path, this is then graphically visualized for the surgeon by means of the control unit. This can take place, for example, in a manner such that a graphical marking is reflected into the field of view and represents the point at present being observed, and simultaneously a further graphical marking is reflected in, corresponding to a point on the actual operation path. This point can be made to travel on the operation path by manual or motorized positioning of the operation microscope. As graphical markings, a line of crosses or the like may be used.

During the operation proper, the operation microscope is now moved by means of the motorized support system along the established operation path. The surgeon can then establish beforehand, in the abovementioned operation planning, both the speed of travel and also given stopping positions, according to requirements.

The speed of travel may be selected according to the present observed field of view or in dependence on the observed region. This means that a significantly slower travel of the operation microscope may take place in given regions of interest of the region of operation.

If the surgeon now needs, at any place of the previously established operation path, the image information from the preoperatively generated diagnostic images, he can at any time call up the previously selected data set and reflect it into the field of view. If a correlation of these images with the present field of view does not then ensue, the surgeon obtains the required positional information from the information, such as image number, which is entered with the image, and from the previously determined image spacings. Moreover a "leafing through" the complete selection of diagnostic images is then possible, i.e., there results an overall improved and more versatile utilization of the preoperative diagnostic data during the operation.

Besides the possibility of undertaking, by means of the process according to the invention, operation planning before the operation proper, there exists also the possibility of modifying this planning, once carried out, during the operation. When, perhaps, the target point once planned has been caused to travel on the originally planned operation path, the operation microscope can now be spatially pivoted in different directions of view about this target point. Other diagnostic images from the diagnostic data set now also correspond to the now altered direction of view to the target point. As already previously described, it is possible for this purpose to select diagnostic images at freely selectable spacings and orientations. In the further travel of the operation microscope along the now modified operation path, the surgeon can, as previously described, observe the selected diagnostic images, reflected into the observation optics of the operation microscope, selectively and independently of the present position of the field of view. Thus the intra-operative utilization of the process according to the invention is also possible.

We claim:

1. Process for operating an operation microscope (1), having observation optics and arranged on a motorized support system (2), in computer-supported stereotactic surgery, comprising:

generating a diagnostic data set by means of an image-forming preoperative diagnostic procedure, storing said diagnostic data set in digitized form in an image database (4), planning a surgical operation on a central control unit (3) by means of said diagnostic data set, thereby establishing an operation path (10), selecting two-dimensional diagnostic images according to said operation path (10) from said diagnostic data set at freely selectable spacings and orientations, causing said operation microscope (1) to travel along said operation path (10) in a defined, motorized manner during said surgical operation and selectively reflecting said diagnostic images into said observation optics of said operation microscope (1) independently of the position of the field of view of said operation microscope (1).

2. Process according to claim 1, further comprising manipulating and storing said diagnostic images after establishing said operation path (10), and manipulating said diagnostic images during said surgical operation for reflection into said observation optics of said operation microscope (1).

3. Process according to claim 2, further comprising drawing contours (11) on said diagnostic images during said manipulation of said diagnostic images to correspond to given anatomical details.

4. Process according to claim 1, further comprising reflecting selected position information for each of said diagnostic images into said observation optics of said operation microscope (1), together with said diagnostic images, to facilitate assignment according to position of a respective diagnostic image according to said operation path (10).

5. Process according to claim 4, wherein said diagnostic images are selected at selectable spacings from each other along said operation path (10), and the spacing from a preceding and succeeding image is reflected into said observation optics of said operation microscope (1) together with each diagnostic image as positional information during said surgical operation.

6. Process according to claim 1, further comprising storing additional patient-specific information together with said diagnostic images and reflecting said additional information into said observation optics of said operation microscope (1) in information fields (12) in said diagnostic images, during said surgical operation.

7. Process according to claim 6, further comprising reflecting into said observation optics of said operation microscope (1) intra-operative responses to stimulation procedures in suitable graphical form.

8. Process according to claim 1, further comprising representing said diagnostic images on at least one monitor (5) during said surgical operation.

9. Process according to claim 1, further comprising selecting between a superimposed representation of an observed field of view and said diagnostic images, and merely a representation of said diagnostic images in said observation optics of said operation microscope (1) during said surgical operation.

10. Process according to claim 1, further comprising selecting the travel speed of said operation microscope (1) along said operation path (10) during said planning step, depending upon the respective positions of the field of view of said operation microscope as observed by the operating surgeon.

* * * * *